US009499646B2

(12) United States Patent
Yamashita et al.

(10) Patent No.: US 9,499,646 B2
(45) Date of Patent: Nov. 22, 2016

(54) NEGATIVE RESIST COMPOSITION, METHOD OF FORMING RESIST PATTERN AND COMPLEX (71) Applicant: TOKYO OHKA KOGYO CO., LTD., Kawasaki (JP)

(72) Inventors: Naoki Yamashita, Kawasaki (JP); Yoshitaka Komuro, Kawasaki (JP); Yoshiyuki Utsumi, Kawasaki (JP); Daiju Shiono, Kawasaki (JP)

(73) Assignee: TOKYO OHKA KOGYO CO., LTD., Kawasaki-Shi (JP)

(*) Notice: Subject to any disclaimer, the term of this patent is extended or adjusted under 35 U.S.C. 154(b) by 0 days.

(21) Appl. No.: 15/153,044

(22) Filed: May 12, 2016

(65) Prior Publication Data
US 2016/0259244 A1 Sep. 8, 2016

Related U.S. Application Data (63) Continuation of application No. 14/558,977, filed on Dec. 3, 2014, now Pat. No. 9,366,960.

(30) Foreign Application Priority Data

Dec. 5, 2013 (JP) ................. 2013-252469

(51) Int. Cl.
*C08F 30/04* (2006.01)
*C07F 7/00* (2006.01)
(Continued)

(52) U.S. Cl.
CPC .............. *C08F 30/04* (2013.01); *C07F 7/006* (2013.01); *C08F 4/06* (2013.01); *C08F 4/12* (2013.01);
(Continued)

(58) Field of Classification Search
CPC ..... G03F 7/004; C08G 18/222; C08F 30/04; C08F 299/0464; C08F 4/06; C08F 4/12; C08F 4/16
USPC ...... 430/270.1; 522/153; 526/240, 241, 319, 526/321
See application file for complete search history.

(56) References Cited

U.S. PATENT DOCUMENTS

| 4,748,087 A | 5/1988 | Davidson et al. |
| 6,512,037 B1 | 1/2003 | Ahn et al. |

(Continued)

FOREIGN PATENT DOCUMENTS

| JP | 58-164608 A | 9/1983 |
| JP | 2003-241385 A | 8/2003 |

(Continued)

OTHER PUBLICATIONS

Cardineau et al., Tightly-Bound Ligands for Hafnium Nanoparticles EUV Resists, Extreme Ultraviolet (EUV) Lithography III, Proceedings of SPIE, vol. 8322, pp. 83220V-1-83220V-10, 2012.

*Primary Examiner* — Amanda C Walke
(74) *Attorney, Agent, or Firm* — Knobbe Martens Olson & Bear LLP (57) ABSTRACT A negative resist composition including a complex represented by the general formula (1); and a polymerization initiator, in which M represents hafnium (Hf) or zirconium (Zr), X represents a ligand comprising a conjugate base of an acid which has an acid dissociation constant (pKa) of 3.8 or less and has a polymerizable group, Y represents a ligand having no polymerizable group, and n represents an integer of 1 to 4.

$$[MX_nY_{4-n}] \quad (1)$$

20 Claims, 1 Drawing Sheet (51) Int. Cl.

| | | |
|---|---|---|
| *C08G 18/22* | (2006.01) | |
| *C08F 4/12* | (2006.01) | |
| *C08F 4/06* | (2006.01) | |
| *C08F 4/16* | (2006.01) | |
| *C08F 299/04* | (2006.01) | |
| *G03F 7/004* | (2006.01) | |

(52) U.S. Cl.
CPC .............. *C08F 4/16* (2013.01); *C08G 18/222* (2013.01); *C08F 299/0464* (2013.01); *G03F 7/004* (2013.01)

(56) References Cited

U.S. PATENT DOCUMENTS

| | | |
|---|---|---|
| 7,083,831 B1 | 8/2006 | Koch et al. |
| 7,560,580 B2 | 7/2009 | Shin et al. |
| 7,629,424 B2 | 12/2009 | Malik et al. |
| 7,888,441 B2 | 2/2011 | Schwab |
| 8,119,248 B2 | 2/2012 | Sawada et al. |
| 8,802,346 B2 | 8/2014 | Malik et al. |
| 2004/0110085 A1 | 6/2004 | Iwai et al. |
| 2009/0250218 A1 | 10/2009 | Akarsu et al. |
| 2010/0168357 A1 | 7/2010 | Khabashesku et al. |
| 2011/0092653 A1 | 4/2011 | Schwab |
| 2011/0143015 A1 | 6/2011 | Morosawa et al. |
| 2011/0184139 A1 | 7/2011 | Malik et al. |
| 2012/0208125 A1 | 8/2012 | Hatakeyama |
| 2013/0023685 A1 | 1/2013 | Lehmann et al. |
| 2013/0168597 A1 | 7/2013 | Houbertz-Krauss et al. |
| 2013/0277627 A1 | 10/2013 | Tseng et al. |
| 2014/0087066 A1 | 3/2014 | Wang et al. |
| 2015/0024522 A1 | 1/2015 | Wang et al. |
| 2015/158966 A1 | 6/2015 | Laas et al. |

FOREIGN PATENT DOCUMENTS

| | | |
|---|---|---|
| JP | 2009-025723 A | 2/2009 |
| JP | 2011-081273 A | 4/2011 |
| JP | 2011-123463 A | 6/2011 |

FIG. 1

NEGATIVE RESIST COMPOSITION, METHOD OF FORMING RESIST PATTERN AND COMPLEX

RELATED APPLICATIONS

This application is a continuation of U.S. patent application Ser. No. 14/558,977, filed Dec. 3, 2014, which claims priority to Japanese Patent Application No. 2013-252469, filed Dec. 5, 2013, the content of which is incorporated herein by reference.

TECHNICAL FIELD

The present invention relates to a negative resist composition, a method of forming a resist pattern, and a complex.

DESCRIPTION OF RELATED ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production. Furthermore, research is also being conducted into lithography techniques that use an exposure light source having a wavelength shorter (energy higher) than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified composition is conventionally used, which includes a base material component that exhibits a changed solubility in a developing solution under the action of acid and an acid-generator component that generates acid upon exposure.

For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If a resist film formed using such a resist composition is selectively exposed at the time of forming a resist pattern, in exposed areas, an acid is generated from the acid generator component, and the polarity of the base resin increases by the action of the generated acid, thereby making the exposed areas soluble in the alkali developing solution. Thus, by conducting alkali developing, the unexposed portions remain to form a positive resist pattern. On the other hand, in the case of applying a solvent developing process using a developing solution containing an organic solvent (organic developing solution), when the polarity of the base resin increases, the solubility in the organic developing solution is relatively decreased. Therefore, unexposed areas of the resist film are dissolved in and removed by the organic developing solution, whereby a negative-type resist pattern in which exposed areas remain as a pattern is formed. Such a solvent developing process for forming a negative resist composition is sometimes referred to as "negative developing process" (for example, see Patent Document 1).

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm (for example, see Patent Document 2).

Incidentally, a lithography process using an electron beam or EUV is different from a general photolithography in respect of reaction mechanism. Regarding a resist pattern to be formed by the lithography process using electron beam or EUV, the target of miniaturization is the formation of a fine pattern having a size of several tens of nanometers.

As the size of a resist pattern becomes smaller, a resist composition that exhibits higher sensitivity to the exposure source is required. Further, as miniaturization of resist patterns progress, the thickness of the resist film formed is also miniaturized. For example, in an electron beam or EUV application, a film thickness of no more than 60 nm has been considered. In this situation, it is important to suppress thickness loss of the resist film following exposure and development of the resist film. For example, in the case of a resist composition of a positive type, the unexposed portions of a resist film are not removed by developing, so that the unexposed portions remain. As a result of thickness loss, uneven portions are generated on the upper surface of the resist pattern, and inferior effects are likely to be caused on the resolution and the pattern shape. In addition, a satisfactory height of the resist pattern cannot be obtained, and it becomes highly possible that the resist pattern does not function as an etching mask in the formation of a semiconductor device.

For solving these problems, there is proposed a resist composition containing, as a base resin, an acrylic resin having in its main chain a structural unit having an acid dissociable dissolution inhibiting group which has a bulky naphthalene ring and a relatively easily dissociable structure (Patent Document 3).

DOCUMENTS OF RELATED ART

Patent Literature

[Patent Literature 1] Japanese Unexamined Patent Application, First Publication No. 2009-025723
[Patent Document 2] Japanese Unexamined Patent Application, First Publication No. 2003-241385
[Patent Document 3] Japanese Unexamined Patent Application, First Publication No. 2011-123463

SUMMARY OF THE INVENTION

Especially, in the case of a lithography process using EUV, a higher sensitivity of a resist composition is required for improving the throughput.

As a base component of a resist composition, an acrylic resin, which is an organic compound, or the like is generally used. However, the generally used acrylic resin or the like has a low EUV light absorption.

In contrast, it is known that metals such as hafnium (Hf) and zirconium (Zr) have an EUV light absorption which is higher than that of carbon atom. However, in the case of a resist composition containing, as a base component, a complex containing the above-mentioned metal(s) (i.e., metal complex), such a resist composition has a poor temporal stability so that it is difficult to obtain resist patterns stably over time.

The present invention has been made in view of the aforementioned circumstances, with an object of providing a resist composition containing a metal having a high EUV light absorption, which has a good temporal stability.

The stability of the structure of a metal complex containing hafnium (Hf) or zirconium (Zr) greatly varies depending on a ligand coordinating to a metal positioned at the center of the complex. As a result of the studies of the present inventors, they have found that, by choosing as a ligand a conjugate base of an acid which has a specific acid dissociation constant (pKa), the structure of the metal complex can be stabilized and the above-mentioned problems can be solved. The present invention has been completed based on this finding.

The negative resist composition according to a first aspect of the present invention comprises a complex represented by the general formula (1), and a polymerization initiator.

$$[MX_nY_{4-n}] \quad (1)$$

wherein M represents hafnium (Hf) or zirconium (Zr), X represents a ligand comprising a conjugate base of an acid which has an acid dissociation constant (pKa) of 3.8 or less and has a polymerizable group, Y represents a ligand having no polymerizable group, and n represents an integer of 1 to 4.

The method of forming a resist pattern according to the second aspect of the present invention comprises: forming a resist film on a substrate using a negative resist composition according to the first aspect of the present invention; exposing the resist film; and developing the exposed resist film to form a resist pattern.

The complex according to the third aspect of the present invention is a complex represented by general formula (1) shown below.

$$[MX_nY_{4-n}] \quad (1)$$

wherein M represents hafnium (Hf) or zirconium (Zr), X represents a ligand comprising a conjugate base of an acid which has an acid dissociation constant (pKa) of 3.8 or less and has a polymerizable group, Y represents a ligand having no polymerizable group, and n represents an integer of 1 to 4.

According to the present invention, there are provided a resist composition containing a metal having a high EUV light absorption, which has a good temporal stability, a method of forming a resist pattern using the resist composition, and a complex useful for the resist composition.

DETAILED DESCRIPTION OF THE INVENTION

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified. The same applies for the alkyl group within an alkoxy group.

The term "alkylene group" includes linear, branched or cyclic, divalent saturated hydrocarbon, unless otherwise specified.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with a fluorine atom.

The term "structural unit" refers to a monomer unit that contributes to the formation of a polymeric compound (resin, polymer, copolymer).

The expression "may have a substituent" means a case where a hydrogen atom (—H) is substituted with a monovalent group, or a case where a methylene (—CH$_2$—) group is substituted with a divalent group.

The term "exposure" is used as a general concept that includes irradiation with any form of radiation.

A "structural unit derived from an acrylate ester" refers to a structural unit that is formed by the cleavage of the ethylenic double bond of an acrylate ester.

An "acrylate ester" refers to a compound in which the terminal hydrogen atom of the carboxy group of acrylic acid (CH$_2$=CH—COOH) has been substituted with an organic group.

The acrylate ester may have the hydrogen atom bonded to the carbon atom on the α-position substituted with a substituent. The substituent (R$^{\alpha 0}$) that substitutes the hydrogen atom bonded to the carbon atom on the α-position is an atom other than hydrogen or a group, and examples thereof include an alkyl group of 1 to 5 carbon atoms and a halogenated alkyl group of 1 to 5 carbon atoms. Further, the aforementioned acrylate ester also include an acrylate ester having the hydrogen atom bonded to the carbon atom on the α-position substituted with a substituent (R$^{\alpha 0}$) in which the substituent has been substituted with a substituent containing an ester bond (e.g., an itaconic acid diester), or in which the substituent has been substituted with a hydroxyalkyl group or a group in which the hydroxy group within a hydroxyalkyl group has been modified (e.g., α-hydroxyalkyl acrylate ester). A carbon atom on the α-position of an acrylate ester refers to the carbon atom bonded to the carbonyl group of acrylic acid, unless specified otherwise.

Hereafter, an acrylate ester having the hydrogen atom bonded to the carbon atom on the α-position substituted with a substituent is sometimes referred to as "α-substituted acrylate ester". Further, acrylate esters and α-substituted acrylate esters are sometimes collectively referred to as "(α-substituted) acrylate ester".

The term "styrene" is a concept including styrene and compounds in which the hydrogen atom at the α-position of styrene is substituted with other substituent such as an alkyl group and a halogenated alkyl group.

A "structural unit derived from styrene" or "structural unit derived from a styrene derivative" refers to a structural unit that is formed by the cleavage of the ethylenic double bond of styrene or a styrene derivative.

As the alkyl group as a substituent on the α-position, a linear or branched alkyl group is preferable, and specific examples include alkyl groups of 1 to 5 carbon atoms, such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group as the substituent on the α-position include groups in which part or all of the hydrogen atoms of the aforementioned "alkyl group as the substituent on the α-position" are substituted with halogen atoms. Examples of the halogen atom include a fluorine atom, a chlorine atom, a bromine atom and an iodine atom, and a fluorine atom is particularly desirable.

Specific examples of the hydroxyalkyl group as the substituent on the α-position include groups in which part or all of the hydrogen atoms of the aforementioned "alkyl group as the substituent on the α-position" are substituted with a hydroxy group. The number of hydroxy groups within the hydroxyalkyl group is preferably 1 to 5, and most preferably 1.

The term "(meth)acrylate ester" is a generic term that includes either or both of the acrylate ester having a hydrogen atom bonded to the α-position and the methacrylate ester having a methyl group bonded to the α-position.

The term "(meth)acrylate" is a generic term that includes either or both of the acrylate having a hydrogen atom bonded to the α-position and the methacrylate having a methyl group bonded to the α-position.

The term "(meth)acrylic acid" is a generic term that includes either or both of acrylic acid having a hydrogen atom bonded to the α-position and methacrylic acid having a methyl group bonded to the α-position.

<<Negative Resist Composition>>

The negative resist composition according to a first aspect of the present invention comprises a complex represented by the general formula (1), a polymerization initiator and, if necessary, other components.

When such a negative resist composition which is soluble in a developing solution is used to form a resist film comprising the complex and the polymerization initiator and the formed resist film is subjected to a selective exposure, polymerization of the metal complex molecules proceeds at exposed portions of the resist film to change the solubility of the exposed portions to a developing solution, whereas the solubility to a developing solution does not change at unexposed portions of the resist film, thereby generating difference in solubility to a developing solution between the exposed portions and the unexposed portions. As a result, by developing the resist film, the unexposed portions are dissolved away while retaining the film at the exposed portions, thereby forming a negative resist pattern.

In the present invention, a resist composition for forming a resist film which is dissolved away at the unexposed portions to form a negative resist pattern is referred to as a negative resist composition.

<Complex>

The negative resist composition of the present embodiment comprises a complex represented by general formula (1) shown below.

The complex has a capability to form a resist film and is polymerizable in the presence of a polymerization initiator.

$$[MX_nY_{4-n}] \quad (1)$$

wherein M represents hafnium (Hf) or zirconium (Zr), X represents a ligand comprising a conjugate base of an acid which has an acid dissociation constant (pKa) of 3.8 or less and has a polymerizable group, Y represents a ligand having no polymerizable group, and n represents an integer of 1 to 4.

In the formula (1), M represents hafnium (Hf) or zirconium (Zr).

In the formula (1), X represents a ligand comprising a conjugate base of an acid which has an acid dissociation constant (pKa) of 3.8 or less and has a polymerizable group.

The "ligand" means an atom or a group of atoms which is or are coordinate-bonded to the central atom (Hf, Zr) of the complex.

A "polymerizable group" refers to a group that renders a compound containing the group polymerizable by a radical polymerization or the like, for example, a group having a carbon-carbon multiple bond such as an ethylenic double bond.

Specific examples include a vinyl group, an allyl group, an acryloyl group, a methacryloyl group, an acryloyloxy group, a methacryloyloxy group, an acrylamide group, a methacrylamide group, an acryloyl aryl group, a methacryloyl aryl group and a norbornyl group.

In the present invention, an "acid dissociation constant (pKa)" refers to a parameter generally used as an index for the acid strength of an objective substance. The pKa value can also be determined by a conventional method. Alternatively, the pKa value can be calculated by simulation using a conventional software such as "ACD/Labs" (trade name; manufactured by Advanced Chemistry Development, Inc.). Further, the pKa value may be one described in literatures.

The pKa value of an acid corresponding to the conjugate base of X is 3.8 or less, preferably 3.5 or less, more preferably 3.0 or less, and still more preferably 2.8 or less. The lower limit is not particularly limited but, for example, is −10 or more. When the pKa value of the acid is within the above-mentioned range, the structure of the metal complex can be stabilized and the temporal stability of the resist composition can be improved.

As an example of X in the formula (1), there can be mentioned a ligand comprising a conjugate base represented by general formula (2) or (3) shown below.

$$R^1\text{—}Y^1\text{—}SO_3^{\ominus} \quad (2)$$

$$R^2\text{—}Y^2\text{—}COO^{\ominus} \quad (3)$$

wherein, in formula (2), $R^1$ represents a polymerizable group having a group selected from groups respectively represented by formulae (X-01) to (X-07) shown below, and $Y^1$ represents a divalent linking group or a single bond; and in formula (3), $R^2$ represents a polymerizable group having a group selected from groups respectively represented by formulae (X-01) to (X-07) shown below, and $Y^2$ represents a divalent linking group or a single bond.

(X-01)

-continued (X-02)

(X-03)

(X-04)

(X-05)

(X-06)

(X-07)

wherein R represents a hydrogen atom, an alkyl group of 1 to 5 carbon atoms or a halogenated alkyl group of 1 to 5 carbon atoms, Ar represents an aromatic hydrocarbon group, n represents an integer of 0 to 2, and * represents a valence bond.

In the formula (2), $R^1$ represents a polymerizable group having a group selected from groups respectively represented by formulae (X-01) to (X-07) shown below.

In the formulae (X-01) to (X-07), R represents a hydrogen atom, an alkyl group of 1 to 5 carbon atoms or a halogenated alkyl group of 1 to 5 carbon atoms. As the alkyl group of 1 to 5 carbon atoms for R, a linear or branched alkyl group of 1 to 5 carbon atoms is preferable, and specific examples thereof include a methyl group, an ethyl group, a propyl group, an isopropyl group, an n-butyl group, an isobutyl group, a tert-butyl group, a pentyl group, an isopentyl group and a neopentyl group. The fluorinated alkyl group of 1 to 5 carbon atoms is a group in which a part or all of the hydrogen atoms within the alkyl group of 1 to 5 carbon atoms have been substituted with a fluorine atom.

In the formula (X-04), the aromatic hydrocarbon group for Ar is a divalent hydrocarbon group having at least one aromatic ring. The aromatic ring is not particularly limited, as long as it is a cyclic conjugated compound having (4n+2) π electrons, and may be either monocyclic or polycyclic. The aromatic ring preferably has 5 to 30 carbon atoms, more preferably 5 to 20, still more preferably 6 to 15, and most preferably 6 to 12. Examples of the aromatic ring include aromatic hydrocarbon rings, such as benzene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom. Specific examples of the aromatic hetero ring include a pyridine ring and a thiophene ring. Specific examples of the aromatic hydrocarbon group for Ar include a group in which two hydrogen atoms have been removed from the aforementioned aromatic hydrocarbon ring or aromatic hetero ring (arylene group or heteroarylene group); a group in which two hydrogen atoms have been removed from an aromatic compound having two or more aromatic rings (biphenyl, fluorene or the like); and a group in which one hydrogen atom of the aforementioned aromatic hydrocarbon ring or aromatic hetero ring has been substituted with an alkylene group (a group in which one hydrogen atom has been removed from the aryl group within the aforementioned arylalkyl group such as a benzyl group, a phenethyl group, a 1-naphthylmethyl group, a 2-naphthylmethyl group, a 1-naphthylethyl group, or a 2-naphthylethyl group). The alkylene group which is bonded to the aforementioned aromatic hydrocarbon ring or the aromatic hetero ring preferably has 1 to 4 carbon atoms, more preferably 1 or 2 carbon atoms, and most preferably 1 carbon atom.

In formula (X-07), n represents an integer of 0 to 2.

In formula (2), $Y^1$ represents a divalent linking group or a single bond.

Examples of the divalent linking group as $Y^1$ include an alkylene group, an arylene group; an alkylene group having an ether bond, an alkylene group having a thioether bond, an alkylene group having an ester bond, and a fluorinated alkylene group.

The alkylene group for $Y^1$ preferably has 1 to 20 carbon atoms, more preferably 1 to 10 carbon atoms, still more preferably 1 to 5 carbon atoms, and specific examples of the alkylene group include a methylene group [—$CH_2$—], an ethylene group [—$(CH_2)_2$—] and a trimethylene group [—$(CH_2)_3$—].

As the arylene group for $Y^1$, the same groups in which two hydrogen atoms have been removed from an aromatic hydrocarbon ring as exemplified in the explanation for Ar in the formula (X-04) can be used.

With respect to the alkylene group having an ether bond, the alkylene group having a thioether bond or the alkylene group having an ester bond for $Y^1$, the alkylene group preferably has 1 to 20 carbon atoms, more preferably 1 to 10 carbon atoms.

With respect to the fluorinated alkylene group for $Y^1$, the alkylene group preferably has 1 to 20 carbon atoms, and more preferably 1 or 10 carbon atoms. The fluorinated alkylene group is a group in which part or all of the hydrogen atoms within an alkylene group have been substituted with a fluorine atom.

Among the above examples of $Y^1$, a methylene group [—$CH_2$—], an ethylene group [—$(CH_2)_2$—], a triethylene group [—$(CH_2)_3$—] are particularly desirable.

Specific examples of the preferred ligand comprising the conjugated base represented by general formula (2) include:

a conjugate base of 3-(methacryloyloxy)-1-propanesulfonic acid (pKa 1.53), a conjugate base of 3-(acryloyloxy)-1-propanesulfonic acid (pKa 1.53), a conjugated base of vinylsulfonic acid (pKa −1.32), and a conjugated base of styrenesulfonic acid (pKa −2.8).

In the formula (3), $R^2$ represents a polymerizable group having a group selected from groups respectively represented by the formulae (X-01) to (X-07), and is the same as mentioned for $R^1$ in the formula (2).

In formula (3), $Y^2$ represents a divalent linking group or a single bond.

Examples of the divalent linking group as $Y^2$ include a methylene group [—$CH_2$—], an arylene group; an alkylene group having an ether bond, an alkylene group having a thioether bond, an alkylene group having an ester bond, and a fluorinated alkylene group.

As the arylene group for $Y^2$, the same groups in which two hydrogen atoms have been removed from an aromatic hydrocarbon ring as exemplified in the explanation for Ar in the aforementioned formula (X-04) can be used.

With respect to the alkylene group having an ether bond, the alkylene group having a thioether bond or the alkylene group having an ester bond for $Y^2$, the alkylene group preferably has 1 to 20 carbon atoms, and more preferably 1 to 10 carbon atoms.

With respect to the fluorinated alkylene group for $Y^2$, the alkylene group preferably has 1 to 20 carbon atoms, and more preferably 1 or 10 carbon atoms. The fluorinated alkylene group is a group in which part or all of the hydrogen atoms within an alkylene group have been substituted with a fluorine atom.

Among the above examples of $Y^2$, a methylene group [—$CH_2$—] is particularly desirable.

Specific examples of the ligand comprising the conjugated base represented by general formula (3) include:

a conjugate base of carboxymethyl methacrylate (pKa 2.53), and a conjugate base of carboxymethyl acrylate (pKa 2.53).

Conjugate bases of carboxylic acids having a specific acid dissociation constant (pKa) exceeding 3.8 as exemplified below are not suited as ligands constituting the complex represented by the general formula (1) and, hence, are not included as X (ligand):

a conjugate base of bicyclo[2.2.1]hept-5-ene-2-carboxylic acid (pKa 4.63), a conjugate base of 2-(acryloxy)-5-oxo-4-oxatricyclo[4.2.1.03,7]nonane-9-carboxylic acid (pKa 4.9), a conjugate base of 5-(bicyclo[2.2.1]hept-5-en-2-ylthio)bicyclo[2.2.1]heptane-2-carboxylic acid (pKa 4.83), a conjugate base of 7-oxabicyclo[4.1.0]heptane-1-carboxylic acid (pKa 4.85), a conjugate base of 7-oxabicyclo[4.1.0]heptane-3-carboxylic acid (pKa 4.82), a conjugate base of 3-oxatricyclo[3.2.1.02,4]octane-6-carboxylic acid (pKa 4.82), and a conjugate base of 3,8-dioxatricyclo[5.1.0.0.2,4]octane-5-carboxylic acid (pKa 4.82).

X in the formula (1) may be one type of ligand or two or more types of ligand.

Especially, from the viewpoint of further improving the temporal stability of the resist composition, X is preferably at least one ligand selected from a ligand comprising the conjugate base represented by the general formula (2) and a ligand comprising a conjugate base represented by the formula (3).

Among these, especially preferred as X is a ligand comprising a conjugate base of at least one acid selected from the group consisting of carboxymethyl acrylate, carboxymethyl methacrylate, 3-(acryloyloxy)-1-propanesulfonic acid and 3-(methacryloyloxy)-1-propane sulfonic acid.

In the formula (1), Y represents a ligand having no polymerizable group.

Specific examples include ligands derived from an oxygen atom, a sulfur atom, a nitrogen atom, a chlorine atom, a methyl group, an ethyl group, an ethylene group, a methoxy group, an ethoxy group, a propoxy group, a butoxy group, an isopropoxy group, a 2-methoxyethoxy group, a 2-ethylhexoxy group, cyclohexanolate, bicyclo[2.2.1]heptane-2-olate, a phenoxy group, a naphthoxy group, methane thiolate, ethane thiolate, propane thiolate, butanethiolate, isopropanethiolate, 2-ethyl hexane thiolate, cyclohexane thiolate, bicyclo[2.2.1]heptanethiolate, benzene thiolate, naphthalene thiolate, acetate, propanoate, butanoate, 2-methyl propanoate, 2-ethyl hexanoate, 2-bromo-5-oxo-4-trioxatricyclo[4.2.1.03,7]nonan-9-carboxylate, 6-(2-naphthylthio)-bicyclo[2.2.1]heptane-2-carboxylate, ethane thioate, propane thioate, butane thioate, 2-methylpropane thioate, 2-ethylhexane thioate, methane sulfonate, ethane sulfonate, propane sulfonate, butane sulfonate, cyclohexane sulfonate, [(1 S,4R)-7,7-dimethyl-2-oxobicyclo[2.2.1]hept-1-yl]methane sulfonate, 4-methylbenzene sulfonate, oxalate, acetoacetonate, 1,3-diphenyl propane-1,3-dione, 2,2,6,6-tetramethylheptane-3,5-dione, 2,2-dimethyl-4, 6-dioxo-1,3-dioxane-5-ide, dicyanomethanide, cyclopenta-2,4-dienide, phenylethenide, nitromethane, nitroethylene, methyl nitrate, phenyl azide, methyl isocyanate, allyl isocyanate, triethylamine, ethylenediamine, triphenylarsine, triphenylphosphine, t-butylphosphine, and trimethylphosphine.

Y in the formula (1) may be one type of ligand or two or more types of ligand.

The above-mentioned Y can be appropriately selected in view of the stability of the complex, the solubility to a solvent, the solubility to a developing solution, the coating property and the like. From the viewpoint of the stability of the complex, it is preferred to use such a ligand that a conjugate base of an acid with pKa of 3.8 or less is formed.

In the formula (1), n represents an integer of 1 to 4, preferably 2 to 4, and more preferably 4.

Specific examples of complex represented by general formula (1) are shown below.

In the negative resist composition of the present embodiment, one type of the complex represented by the general formula (1) may be used, or two or more types of the complex may be used in combination.

In the negative resist composition of the present embodiment, the amount of the complex represented by the general formula (1) can be appropriately adjusted depending on the thickness of the resist film to be formed, and the like. For example, the amount of the complex in the solid components of the negative resist composition is preferably 50 to 99.5% by weight, more preferably 70 to 99% by weight, and still more preferably 80 to 97% by weight. Further, in the negative resist composition, the amount of the complex relative to, for example, the total weight of the complex, the polymerization initiator and other components (optional components) is preferably 50 to 99.5% by weight, more preferably 70 to 99% by weight, and still more preferably 80 to 97% by weight.

<Polymerization Initiator>

In the negative resist composition of the present embodiment, the polymerization initiator is not particularly limited as long as it can initiate polymerization reaction of the complex by exposure, and conventionally known photopolymerization initiators and the like can be used.

Examples of the polymerization initiator include benzyl, bis(4-dimethylaminophenyl) ketone, 1-hydroxycyclohexyl phenyl ketone; α-diketones such as diacetyl; acyloin such as benzoin; acyloin ethers such as benzoin methyl ether, benzoin ethyl ether, benzoin isopropyl ether, benzoin-n-butyl ether, benzoin isobutyl ether; thioxanthone, 2-methyl thioxanthone, 2-isopropyl thioxanthone, 2,4-dimethyl thioxanthone, 2,4-diethyl thioxanthone, 2-chloro thioxanthone, 1-chloro-4-propoxy thioxanthone, and thioxanthone-4-sulfonic acid; thioxanthene, 2-chlorothioxanthene, 2,4-diethylthioxanthene, 2-methylthioxanthene, and 2-isopropylthioxanthene; benzophenones such as benzophenone, 4,4'-bis(dimethylamino) benzophenone, 4,4'-bis(diethylamino)benzophenone, 3,3-dimethyl-4-methoxy benzophenone, 2-chlorobenzophenone, and 4,4'-dichlorobenzophenone; acetophenones such as acetophenone, p-dimethylaminoacetophenone, α, α'-dimethoxyacetoxybenzophenone, 2,2-diethoxyacetophenone, 2,2'-dimethoxy-2-phenylacetophenone, p-methoxyacetophenone, p-tert-butyl-acetophenone, p-tert-butyldichloroacetophenone, p-tert-butyl-trichloroacetophenone, α, α-dichloro-4-phenoxyacetophenone, 2-methyl [4-(methylthio)phenyl]-2-morpholino-1-propanone, 2-benzyl-2-dimethylamino-1-(4-morpholinophenyl)-butane-1-one, p-dimethylaminopropiophenone, dichloroacetophenone, and trichloroacetophenone; quinones such as anthraquinone, 2-ethyl anthraquinone, octamethylanthraquinone, 1,2-benzanthraquinone, 2,3-diphenylanthraquinone, and 1,4-naphthoquinone; halogen compounds such as phenacyl chloride, tribromomethylphenylsulfone, p-methoxy triazine, 2-methyl-4,6-bis(trichloromethyl)-s-triazine, tris(trichloromethyl)-s-triazine, 2,4-bis-trichloromethyl-6-(3-bromo-4-methoxy)phenyl-s-triazine, 2,4-bis-trichloromethyl-6-(2-bromo-4-methoxy) phenyl-s-triazine, 2,4-bis-trichloromethyl-6-(3-bromo-4-methoxy)styrylphenyl-s-triazine, 2,4-bis-trichloromethyl-6-(2-bromo-4-methoxy) styrylphenyl-s-triazine, 2-[2-(5-methyl-furan-2-yl)ethenyl]-4,6-bis (trichloromethyl)-s-triazine, 2-[2-(furan-2-yl) ethenyl]-4,6 bis(trichloromethyl)-s-triazine, 2-[2-(4-diethylamino-2-methylphenyl)ethenyl]-4,6-bis (trichloromethyl)-s-triazine, 2-[2-(3, 4-dimethoxyphenyl) ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, and 2-(4-n-butoxyphenyl)-4,6-bis(trichloromethyl)-s-triazine; acyl phosphine oxides such as 2,4,6-trimethylbenzoyldiphenylphosphine oxide, bis(2,6-dimethoxybenzoyl)-2,4,4-trimethyl-pentylphosphine oxide, and bis(2,4,6-trimethylbenzoyl)phenylphosphine oxide; peroxides such as di-t-butyl peroxide, benzoyl peroxide, and cumene peroxide; 1-[4-(2-hydroxyethoxy)phenyl]-2-hydroxy-2-methyl-1-propane-1-one, 1-(4-isopropylphenyl)-2-hydroxy-2-methylpropane-1-one, 1-(4-dodecylphenyl)-2-hydroxy-2-methylpropane-1-one, 2-hydroxy-2-methyl-1-phenylpropane-1-one, 2,2-dimethoxy-1,2-diphenylethane-1-one, and ethanone; 4-benzoyl-4'-methyldimethyl sulfide, 4-dimethylaminobenzoic acid, methyl 4-dimethylaminobenzoate, ethyl 4-dimethylaminobenzoate, butyl 4-dimethylaminobenzoate, 2-ethylhexyl 4-dimethylaminobenzoate, 2-isoamyl 4-dimethylaminobenzoate-, and methyl o-benzoylbenzoate; benzyl dimethyl ketal, benzyl-β-methoxyethyl acetal, 1-[9-ethyl-6-(2-methyl-benzoyl)-9H-carbazol-3-yl], 1-phenyl-1, 2-propanedione-2-(o-ethoxycarbonyl) oxime, 1-(o-acetyl oxime), dibenzosuberone, pentyl-4-dimethylaminobenzoate; 2-mercaptobenzoimidazole, 2-mercaptobenzoxazole, and 2-mercaptobenzothiazole; 2-(o-chlorophenyl)-4,5-diphenyl imidazolyl dimer, 2-(o-chlorophenyl)-4,5-di (methoxyphenyl)imidazole dimer, 2-(o-fluorophenyl)-4,5-diphenyl imidazole dimer, 2-(o-methoxyphenyl)-4,5-diphenyl imidazole dimer, 2-(p-methoxyphenyl)-4,5-diphenylimidazole dimer, and 2,4,5-triarylimidazole dimer; azobisisobutyronitrile, 9-phenyl acridine, 1,7-bis-(9-acridinyl) heptane, 1,5-bis-(9-acridinyl) pentane, and 1,3-bis-(9-acridinyl)propane.

In the negative resist composition of the present embodiment, one type of polymerization initiator may be used, or two or more types of polymerization initiators may be used in combination.

Among the above examples of the polymerization initiator, acetophenones are preferred since the polymerization of the complex can easily proceed.

In the negative resist composition of the present embodiment, the amount of the polymerization initiator is preferably 0.5 to 50 parts by weight, more preferably 1 to 20 parts by weight, and most preferably 1 to 15 parts by weight, relative to 100 parts by weight of the complex. When the amount of the polymerization initiator is within the above-mentioned range, the film-forming property of the negative resist resin composition can be improved, and unsatisfactory curing can be suppressed.

<Optional Components>

The negative resist composition of the present embodiment may comprise, if necessary, other components as well as the complex represented by the general formula (1) and the polymerization initiator.

Examples of the other components include monomers copolymerizable with the complex, surfactants, sensitizers, cure-accelerators, fillers, adhesion promoters, antioxidants, anti-aggregating agents, thermal polymerization inhibitors and defoamers.

Examples of the monomers copolymerizable with the complex include polymerizable monomers such as conventionally known monofunctional monomers and multifunctional monomers, and especially preferred are (meth)acrylate-type polymerizable monomers. As the aforementioned monomer, one type of monomer may be used, or two or more types of monomers may be used in combination. When the monomer copolyermizable with the complex is used, the amount of the copolymerizable monomer in the negative resist composition can be appropriately selected in view of the inorganic property of the resist pattern to be obtained, and the amount is, for example, preferably 10 to 150 parts by weight, relative to 100 parts by weight of the complex.

The negative resist composition of the present embodiment can be produced by a method comprising dissolving a complex represented by the general formula (1), a polymerization initiator and, if necessary, other components in an organic solvent component.

The organic solvent component may be any organic solvent which can dissolve the respective components to give a homogeneous solution, and can be appropriately selected from those which have been conventionally known as solvents for a chemically amplified resist composition.

Examples thereof include lactones such as y-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol, and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzyl ether, cresyl methyl ether, diphenyl ether, dibenzyl ether, phenetole, butyl phenyl ether, ethylbenzene, diethylbenzene, pentylbenzene, isopropylbenzene, toluene, xylene, cymene and mesitylene; and dimethylsulfoxide.

In the negative resist composition of the present embodiment, one type of organic solvent may be used, or two or more types of organic solvents may be used in combination.

Among the aforementioned examples, PGME and EL are preferable.

The amount of the organic solvent component is not particularly limited, and is appropriately adjusted to a concentration which enables coating of a coating solution to a substrate, depending on the desired thickness of the coating. In general, the organic solvent is used in an amount such that the solid content of the resist composition becomes preferably within the range from 1 to 20% by weight, and more preferably from 2 to 15% by weight.

<<Method of Forming a Resist Pattern>>

The method of forming a resist pattern according to the second aspect of the present invention comprises: forming a resist film on a substrate using a negative resist composition according to the first aspect of the present invention; exposing the resist film; and developing the exposed resist film to form a resist pattern.

The method of forming a resist pattern according to the present embodiment can be performed, for example, as follows.

Firstly, the aforementioned negative resist composition is applied to a substrate using a spinner or the like, and a bake treatment (post applied bake (PAB)) is conducted, for example, at a temperature of 80 to 150° C. for 40 to 120 seconds, preferably 60 to 90 seconds, to form a resist film comprising the complex and the polymerization initiator. The thickness of the resist film is preferably within the range from about 10 to about 300 nm, and more preferably from about 20 to about 200 nm.

Subsequently, the resist film is selectively exposed using an exposure apparatus such as an EUV exposure apparatus, either by exposure through a mask having a predetermined pattern formed thereon (mask pattern), or by large area exposure or the like without using a mask pattern.

Then, the baking treatment (post exposure baking (PEB)) is conducted under temperature conditions of 80 to 150° C. for 40 to 120 seconds, and preferably 60 to 90 seconds.

Next, the resist film which has been subjected to the exposure and the baking treatment (PEB) is subjected to a developing treatment.

The developing treatment is conducted using a developing solution to which the unexposed portions of the resist film exhibit solubility and the exposed portions of the resist film do not exhibit solubility.

After the developing treatment, it is preferable to conduct a rinse treatment.

After the developing treatment or the rinse treatment, drying is conducted. If desired, the bake treatment (post bake) can be conducted following the developing treatment.

In this manner, a resist pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

With respect to the wavelength to be used for exposure, the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays. The method of the present invention is useful for exposure with EB or EUV and especially useful for exposure with EUV since the method uses a negative resist composition comprising, as a base component, a metal complex containing hafnium (Hf) or zirconium (Zr) which exhibits higher absorption of EUV light than carbon atom.

The exposure of the resist film can be either a general exposure (dry exposure) conducted in air or an inert gas such as nitrogen, or immersion exposure (liquid immersion lithography).

In liquid immersion lithography, the region between the resist film and the lens at the lowermost point of the exposure apparatus is pre-filled with a solvent (immersion medium) that has a larger refractive index than the refractive index of air, and the exposure (immersion exposure) is conducted in this state.

The immersion medium preferably exhibits a refractive index larger than the refractive index of air but smaller than the refractive index of the resist film to be exposed. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point of preferably 70 to 180° C. and more preferably 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

The developing solution is not particularly limited as long as it can dissolve the resist film before exposure, and a developing solution containing an organic solvent (organic developing solution) is preferably used. The organic solvent contained in the organic developing solution can be appropriately selected from the conventional organic solvents. Specific examples of the organic solvent include polar solvents such as ketone solvents, ester solvents, alcohol solvents, nitrile solvents, amide solvents and ether solvents, and hydrocarbon solvents.

A ketone solvent is an organic solvent containing C—C(=O)—C within the structure thereof. An ester solvent is an organic solvent containing C—C(=O)—O—C within the structure thereof. An alcohol solvent is an organic solvent containing an alcoholic hydroxy group within the structure thereof, and an "alcoholic hydroxy group" refers to a hydroxy group bonded to a carbon atom of an aliphatic hydrocarbon group. As the alcohol solvent, it is preferred to use one in which a hydroxy group is bonded to a carbon atom of an aliphatic hydrocarbon group of 4 or more carbon atoms. A nitrile solvent is an organic solvent containing a nitrile group in the structure thereof. An amide solvent is an organic solvent containing an amide group within the structure thereof. An ether solvent is an organic solvent containing C—O—C within the structure thereof.

Some organic solvents have a plurality of functional groups which characterize the aforementioned solvents within the structure thereof. In such a case, the organic solvent can be classified as any type of the solvent having the characterizing functional group. For example, diethyleneglycol monomethyl ether can be classified as either an alcohol solvent or an ether solvent.

A hydrocarbon solvent consists of a hydrocarbon which may be halogenated, and does not have any substituent other than a halogen atom. Examples of the halogen atom include a fluorine atom, a chlorine atom, a bromine atom and an iodine atom, and a fluorine atom is preferable.

Among the above examples, as the organic solvent, polar solvents are preferable, and ester solvents are especially preferable.

Examples of ester solvents include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl-3-methoxypropionate, ethyl-3-methoxypropionate, ethyl-3-ethoxypropionate and propyl-3-methoxypropionate.

As an ester solvent, ethyl lactate is preferable.

If desired, the organic developing solution may have a conventional additive blended. Examples of the additive include surfactants. The surfactant is not particularly limited, and for example, an ionic or non-ionic fluorine and/or silicon surfactant can be used.

As the surfactant, a non-ionic surfactant is preferable, and a fluorine surfactant or a silicon surfactant is more preferable.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern. In general, at least one solvent selected from the group consisting of hydrocarbon solvents, ketone solvents, ester solvents, alcohol solvents, amide solvents and ether solvents is used. Among these, at least one solvent selected from the group consisting of hydrocarbon solvents, ketone solvents, ester solvents, alcohol solvents and amide solvents is preferable, at least one solvent selected from the group consisting of alcohol solvents and ester solvents is more preferable, and an ester solvent is particularly desirable.

These organic solvents can be used individually, or at least 2 solvents may be mixed together. Further, an organic solvent other than the aforementioned examples or water may be mixed together. However, in consideration of the development characteristics, the amount of water within the rinse liquid, based on the total amount of the rinse liquid is preferably 30% by weight or less, more preferably 10% by weight or less, still more preferably 5% by weight or less, and most preferably 3% by weight or less.

If desired, the rinse solution may have a conventional additive blended. Examples of the additive include surfactants. As the surfactant, the same surfactants as those described above can be mentioned, and a non-ionic surfactant is preferable, and a fluorine surfactant or a silicon surfactant is more preferable.

When a surfactant is added, the amount thereof based on the total amount of the rinse liquid is generally 0.001 to 5% by weight, preferably 0.005 to 2% by weight, and more preferably 0.01 to 0.5% by weight.

The rinse treatment using a rinse liquid (washing treatment) can be conducted by a conventional rinse method. Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

In the aforementioned method for forming a resist pattern according to the present embodiment, the polymerizable groups of ligands in the complex molecules are cleaved by polymerization to cause the complex molecules to be bonded together, and the complex molecules become insoluble to the developing solution by the polymerization thereof so as to form a resist pattern.

Further, since the obtained resist pattern contains a metal (Hf, Zr), the resist pattern has excellent resistance to etching.

<<Complex Represented by the General Formula (1)>>

The complex according to the third aspect of the present invention is a complex represented by general formula (1) shown below, and is the same as the complex represented by the general formula (1) which is explained above in connection with the negative resist composition of the present invention.

$$[MX_nY_{4-n}] \quad (1)$$

wherein M represents hafnium (Hf) or zirconium (Zr), X represents a ligand comprising a conjugate base of an acid which has an acid dissociation constant (pKa) of 3.8 or less and has a polymerizable group, Y represents a ligand having no polymerizable group, and n represents an integer of 1 to 4.

Among the raw materials of the resist composition, the complex of the present embodiment is a compound useful as a raw material (monomer) of a resin component for forming a resist pattern. The complex of the present invention is especially useful as a base component having a resist film-forming ability to be used in a resist composition for lithography using EUV since hafnium (Hf) or zirconium (Zr) contained in the complex exhibits higher absorption of EUV light than carbon atom.

For example, when n in the general formula (1) is 4, the complex of the present embodiment can be produced by a method in which an alkoxide compound of hafnium (Hf) or an alkoxide compound of zirconium (Zr) is mixed with a polymerizable group-containing acid having an acid dissociation constant (pKa) of 3.8 or less in a solvent (e.g., tetrahydrofuran, chloroform and dichloromethane), followed by purification and the like.

When n in the general formula (1) is 1 to 3, the complex of the present embodiment can be produced by a method in which an alkoxide compound of hafnium (Hf) or an alkoxide compound of zirconium (Zr) is mixed with a polymerizable group-containing acid having an acid dissociation constant (pKa) of 3.8 or less and a compound which has no polymerizable group and is capable of forming a ligand in a solvent (e.g., tetrahydrofuran, chloroform and dichloromethane), followed by purification and the like.

Regarding the temperature at which the aforementioned alkoxide, specific acid and, when n is 1 to 3, compound which has no polymerizable group and is capable of forming a ligand, the temperature can be selected in view of the boiling point of the solvent and may be selected within the range of about 20 to about 200° C. Further, the mixing time is preferably 30 minutes to 10 hours.

EXAMPLES

As follows is a description of examples of the present invention, although the scope of the present invention is by no way limited by these examples.

Synthesis of Complex

Synthesis Example 1

In a flask, hafnium butoxide (1.17 g), methacrylic acid (1.27 g) and dichloromethane (20 g) as a solvent were mixed and stirred at room temperature (23° C.) for 60 minutes. The obtained solution was washed with methyl tert-butyl ether (TBME), followed by filtration and drying under reduced pressure for 5 hours, thereby obtaining a complex (Hf-4) (produced amount: 1.26 g, yield: 73.3%).

Figure 1:
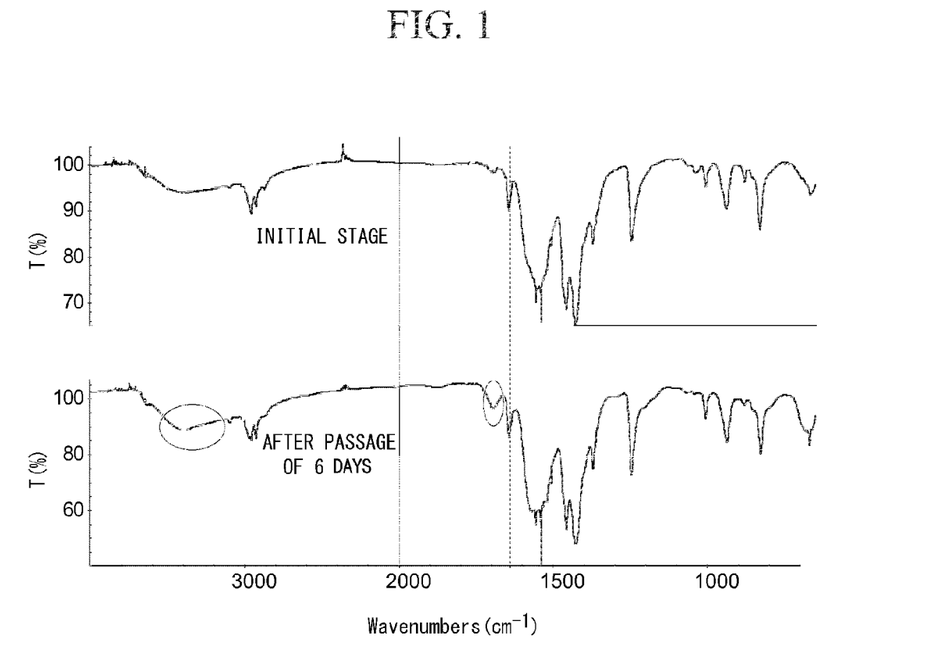
FIG. 1 shows infrared absorption spectra of a negative resist composition of Comparative Example 4 which contains a complex (Hf-4) as measured by the Fourier transform infrared (FTIR) spectroscopy.

As shown in FIG. 1 mentioned below, in the infrared absorption spectra obtained by the Fourier transform infrared (FT-IR) spectroscopy, the peak ascribed to the carbonyl moiety of methacrylic acid (generally observed at 1,700 cm$^{-1}$) was shifted to around 1,600 cm$^{-1}$ (position indicated by the vertical broken line in FIG. 1) (i.e., a shift characteristic of a complex), whereby it was confirmed that the conjugate base of the methacrylic acid coordinates to Hafnium to form a complex (Hf-4).

Complex (Hf-4)

Synthesis Examples 2 to 4

The same procedure as in Synthesis Example 1 was conducted, except that 3-(methacryloyloxy)-1-propanesulfonic acid, carboxymethyl methacrylate and 2-carboxyethyl methacrylate were respectively used instead of methacrylic acid, thereby obtaining a complex (Hf-1), a complex (Hf-2) and a complex (Hf-3).

In the infrared absorption spectra obtained by FT-IR spectroscopy with respect to each of the complexes, a shift of the peak ascribed to the carbonyl moiety of methacryloyl was observed (i.e., a shift characteristic of a complex), whereby it was confirmed that the conjugate bases of the respective acids coordinate to Hafnium atoms to respectively form a complex (Hf-1), a complex (Hf-2) and a complex (Hf-3).

Complex (Hf-1)

Complex (Hf-2)

Complex (Hf-3)

Complex (Zr-1)

Complex (Zr-2)

Synthesis Example 5

The same procedure as in Synthesis Example 1 was conducted, except that hafnium butoxide was replaced by an equimolar amount of zirconium butoxide, thereby obtaining a complex (Zr-4).

Complex (Zr-4)

Complex (Zr-3)

Synthesis Examples 6 to 8

The same procedure as in Synthesis Example 5 was conducted, except that 3-(methacryloyloxy)-1-propanesulfonic acid, carboxymethyl methacrylate and 2-carboxyethyl methacrylate were respectively used instead of methacrylic acid, thereby obtaining a complex (Zr-1), a complex (Zr-2) and a complex (Zr-3).

<Acid Dissociation Constant (pKa)>

The pKa values of the acids used in Synthesis Examples 1 to 8 (i.e., 3-(methacryloyloxy)-1-propanesulfonic acid, carboxymethyl methacrylate, 2-carboxyethyl methacrylate and methacrylic acid) were calculated by "ACD/Labs V11.02" (tradename, manufactured by Advanced Chemistry Development, Inc.). The obtained pKa values are shown below.

pKa1. 53 pKa2. 53 pKa3. 94 pKa4. 58

Production of Negative Resist Composition

Examples 1 to 4

Comparative Examples 1 to 6

The components shown in Tables 1 to 2 were mixed together and dissolved to obtain each negative resist composition.

TABLE 1

| Hf metal | Complex | Polymerization initiator | Organic solvent |
|---|---|---|---|
| Example 1 | (A)-1 [100] | (I)-1 [10] | (S)-1 [1100] |
| Example 2 | (A)-2 | (I)-1 | (S)-1 |

TABLE 1-continued

| Hf metal | Complex | Polymerization initiator | Organic solvent |
|---|---|---|---|
|  | [100] | [10] | [1100] |
| Comparative Example 1 | (A)-3 [100] | (I)-1 [10] | (S)-1 [1100] |
| Comparative Example 2 | (A)-3 [100] | (I)-1 [5] | (S)-1 [1100] |
| Comparative Example 3 | (A)-3 [100] | — | (S)-1 [1100] |
| Comparative Example 4 | (A)-4 [100] | (I)-1 [10] | (S)-1 [1100] |

TABLE 2

| Zr metal | Complex | Polymerization initiator | Organic solvent |
|---|---|---|---|
| Example 3 | (A)-5 [100] | (I)-1 [10] | (S)-1 [1100] |
| Example 4 | (A)-6 [100] | (I)-1 [10] | (S)-1 [1100] |
| Comparative Example 5 | (A)-7 [100] | (I)-1 [10] | (S)-1 [1100] |
| Comparative Example 6 | (A)-8 [100] | (I)-1 [10] | (S)-1 [1100] |

In Tables 1 to 2, the reference characters indicate the following. The values in brackets [ ] indicate the amount (in terms of parts by weight) of the component added.

(A)-1: the aforementioned complex (Hf-1)
(A)-2: the aforementioned complex (Hf-2)
(A)-3: the aforementioned complex (Hf-3)
(A)-4: the aforementioned complex (Hf-4)
(A)-5: the aforementioned complex (Zr-1)
(A)-6: the aforementioned complex (Zr-2)
(A)-7: the aforementioned complex (Zr-3)
(A)-8: the aforementioned complex (Zr-4)
(I)-1: a polymerization initiator represented by chemical formula (I-1) shown below.
(S)-1: propylene glycol monomethyl ether (I-1)

<Evaluation>

Using the obtained negative resist compositions, the film retentiveness of the resist film, the resolution and the temporal stability were evaluated as follows. The results are shown in Table 3, 4 and 5.

[Evaluation of Film Retentiveness]

Using a spinner, the negative resist composition of each of the Examples was applied to an 8-inch silicon wafer that had been treated with hexamethyl disilazane (HMDS) (at 90° C. for 36 seconds), and was then prebaked (PAB) and dried on a hotplate at 110° C. for 60 seconds, thus forming a resist film having a film thickness of 100 nm.

Subsequently, the resist film was irradiated with an ArF excimer laser (193 nm) not via a photomask, using an ArF exposure apparatus NikonNSR-5302 (manufactured by Nikon Corporation; NA (numerical aperture)=0.60, annular). The irradiation with the ArF excimer laser was performed while stepwisely increasing the irradiation level by 2 mJ/cm² at each step within a range of 2 to 100 mJ/cm².

Then, a post exposure bake (PEB) treatment was conducted at 130° C. for 60 seconds.

Next, a solvent development was conducted at 23° C. for 30 seconds using ethyl lactate, followed by drying by shaking.

Then, the thicknesses of the resist films at the respective irradiation levels were confirmed by Nanospec 6100A (manufactured by Nanometrics Inc.), and a residual film curve was plotted. The film retentiveness was evaluated with the following criteria. The results are shown in Table 3.

Criteria

Film retained: The thickness of the resist film after the solvent development and the drying by shaking was 80 nm or more.

No film retained: The film was not cured with the radiation at 2 to 100 mJ, and no resist film was retained after the solvent development and the drying by shaking.

Immediately after the preparation (initial stage) and at 6 days after the preparation, the infrared absorption spectra of the respective compositions were measured by the Fourier transform infrared (FT-IR) spectroscopy, observations were made on the changes of the shape of the spectra (especially, a peak ascribed to hydroxy group ($H_2O$) observed around a wavenumber just exceeding 3,000 cm and a peak ascribed to carbonyl group (C=O) observed around 1,700 $cm^{-1}$).

Then, the temporal stability of the negative resist compositions was evaluated based on the following criteria: "B" (poor temporal stability) when the change of the shape of the spectra was observed by the end of the 6-day term after the preparation; and "A" (good temporal stability) when the change of the shape of the spectra was not observed by the end of the 6-day term after the preparation.

These results are shown in Tables 4 and 5 as "change or no change of shape of spectra" and "temporal stability (after 6 days)".

With respect to each of the negative resist compositions of Examples 1 to 4, no change of shape of spectra was observed

TABLE 3

|  | Ex. 1 | Ex. 2 | Comp. Ex. 1 | Comp. Ex. 2 | Comp. Ex. 3 | Comp. Ex. 4 | Ex. 3 | Ex. 4 | Comp. Ex. 5 | Comp. Ex. 6 |
|---|---|---|---|---|---|---|---|---|---|---|
| Polymerization initiator (Parts by weight) | 10 | 10 | 10 | 5 | 0 | 10 | 10 | 10 | 10 | 10 |
| Film retentiveness | Film retained | Film retained | Film retained | Film retained | No film retained | Film retained | Film retained | Film retained | Film retained | Film retained |

[Evaluation of Resolution]

Using a spinner, the negative resist composition of each of the Examples was applied to an 8-inch silicon wafer that had been treated with HMDS (at 90° C. for 36 seconds), and was then prebaked (PAB) and dried on a hotplate at 110° C. for 60 seconds, thus forming a resist film having a film thickness of 100 nm.

Subsequently, the resist film was irradiated with an ArF excimer laser (193 nm) through a photomask (target size: a line width of 250 nm and a pitch of 500 nm), using an ArF exposure apparatus NikonNSR-S302 (manufactured by Nikon Corporation; NA (numerical aperture)=0.60, annular).

Then, a post exposure bake (PEB) treatment was conducted at 130° C. for 60 seconds.

Next, a solvent development was conducted at 23° C. for 30 seconds using ethyl lactate, followed by drying by shaking.

Then, the resolution was evaluated based on whether or not a predetermined line-and-space resist pattern (250 LS pattern) was formed.

In Tables 4 and 5, "Resolution" indicates that a 250 LS pattern was formed.

[Evaluation of Temporal Stability]

In each of the Examples and Comparative Examples, the negative resist composition prepared was stored at room temperature (23° C.) for 10 days.

even 10 days after the preparation of the composition, thus indicating that the temporal stability of the composition was excellent.

FIG. 1 shows infrared absorption spectra of a negative resist composition of Comparative Example 4 which contains a complex (Hf-4) as measured by the Fourier transform infrared (FT-IR) spectroscopy. With respect to each of the spectra, the ordinate indicates the transmittance (%). In FIG. 1, the infrared absorption at the initial stage and at 6 days after the preparation are shown with the common abscissa.

At 6 days after the preparation, the change of shape of spectra at a wavenumber just exceeding 3,000 $cm^{-1}$ (range circled in FIG. 1) is distinct as compared to the initial stage. This can be ascribed to the hydrolysis that occurred with the lapse of time.

Further, in FIG. 1, the change of spectrum shape is also observed around 1,700 $cm^{-1}$. From the emergence of a peak around 1,700 $cm^{-1}$ (ascribed to the carbonyl group) with the lapse of time, it is presumed that the ligands are dissociated from the complex.

That is, from the results of the evaluation of the temporal stability, it is confirmed that the negative resist composition of Comparative Example 4 is susceptible to temporal structural change of the complex (Hf-4), namely the temporal stability of the composition is poor, so that a resist pattern cannot be stably obtained.

TABLE 4

| Hf metal | | Example 1 | Example 2 | Comparative Example 1 | Comparative Example 4 |
|---|---|---|---|---|---|
| Complex |  | (Hf-1) | (Hf-2) | (Hf-3) | (Hf-4) |
| General Formula (I) | M | Hafnium | Hafnium | Hafnium | Hafnium |

TABLE 4-continued

| Hf metal | | Example 1 | Example 2 | Comparative Example 1 | Comparative Example 4 |
|---|---|---|---|---|---|
| | X | Conjugate base of 3-(methacryloyloxy)-1-propanesulfonic acid (pKa 1.53) | Conjugate base of carboxymethyl methacrylate (pKa 2.53) | Conjugate base of 2-carboxyethyl methacrylate (pKa 3.94) | Conjugate base of methacrylic acid (pKa 4.58) |
| | n | 4 | 4 | 4 | 4 |
| Film retentiveness | | Film retained | Film retained | Film retained | Film retained |
| Resolution of 250 LS pattern | | Resolution | Resolution | Resolution | Resolution |
| Change or no change of shape of spectra | | No change | No change | Changed | Changed |
| Temporal stability (after 6 days) | | A | A | B | B |

TABLE 5

| Zr metal | | Example 3 | Example 4 | Comparative Example 5 | Comparative Example 6 |
|---|---|---|---|---|---|
| Complex General formula (1) | M | (Zr-1) Zirconium | (Zr-2) Zirconium | (Zr-3) Zirconium | (Zr-4) Zirconium |
| | X | Conjugate base of 3-(methacryloyloxy)-1-propanesulfonic acid (pKa 1.53) | Conjugate base of carboxymethyl methacrylate (pKa 2.53) | Conjugate base of 2-carboxyethyl methacrylate (pKa 3.94) | Conjugate base of methacrylic acid (pKa 4.58) |
| | n | 4 | 4 | 4 | 4 |
| Film retentiveness | | Film retained | Film retained | Film retained | Film retained |
| Resolution of 250 LS pattern | | Resolution | Resolution | Resolution | Resolution |
| Change or no change of shape of spectra | | No change | No change | Changed | Changed |
| Temporal stability (after 6 days) | | A | A | B | B |

From the aforementioned results of the evaluations, it is apparent that the negative resist compositions of Examples 1 to 4 according to the present invention, each containing a metal (Hf, Zr) having a high EUV light absorption, have a good temporal stability.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A complex which is represented by the following general formula (1):

[MX$_n$Y$_{4-n}$]  (1)

wherein M represents hafnium or zirconium, X represents a ligand comprising a conjugate base of an acid which has an acid dissociation constant pKa of 3.8 or less and has a polymerizable group, Y represents a ligand having no polymerizable group, and n represents an integer of 1 to 4.

2. The complex according to claim 1, wherein the acid dissociation constant pKa of the acid is 2.8 or less.

3. The complex according to claim 1, wherein X in the formula (1) is a ligand comprising a conjugate base represented by general formula (2) shown below:

R$^1$—Y$^1$—SO$_3$$^\ominus$  (2)

wherein R$^1$ represents a polymerizable group having a group selected from groups (X-01) to (X-07) shown below, and Y$^1$ represents a divalent linking group or a single bond;

(X-01)

(X-02)

wherein R represents a hydrogen atom, an alkyl group of 1 to 5 carbon atoms or a halogenated alkyl group of 1 to 5 carbon atoms, Ar represents an aromatic hydrocarbon group, n represents an integer of 0 to 2, and * represents a valence bond.

4. The complex according to claim 1, wherein X in the formula (1) is a ligand comprising a conjugate base selected from the group consisting of a conjugate base of 3-(methacryloyloxy)-1-propanesulfonic acid, a conjugate base of 3-(acryloyloxy)-1-propanesulfonic acid, a conjugated base of vinylsulfonic acid, and a conjugated base of styrenesulfonic acid.

5. The complex according to claim 1, wherein X in the formula (1) is a ligand comprising a conjugate base represented by general formula (3) shown below:

$$R^2\text{—}Y^2\text{—}COO^{\ominus} \quad (3)$$

wherein, in formula (3), $R^2$ represents a polymerizable group having a group selected from (X-01) to (X-07) shown below, and $Y^2$ represents a divalent linking group or a single bond:

wherein R represents a hydrogen atom, an alkyl group of 1 to 5 carbon atoms or a halogenated alkyl group of 1 to 5 carbon atoms, Ar represents an aromatic hydrocarbon group, n represents an integer of 0 to 2, and * represents a valence bond.

6. The complex according to claim 1, wherein X in the formula (1) is a ligand comprising a conjugate base selected from the group consisting of a conjugate base of carboxymethyl methacrylate, and a conjugate base of carboxymethyl acrylate.

7. The complex according to claim 1, wherein M represents hafnium.

8. The complex according to claim 2, wherein M represents hafnium.

9. The complex according to claim 3, wherein M represents hafnium.

10. The complex according to claim 4, wherein M represents hafnium.

11. The complex according to claim 5, wherein M represents hafnium.

12. The complex according to claim 6, wherein M represents hafnium.

13. The complex according to claim 1, wherein M represents zirconium.

14. The complex according to claim 2, wherein M represents zirconium.

15. The complex according to claim 3, wherein M represents zirconium.

16. The complex according to claim 4, wherein M represents zirconium.

17. The complex according to claim 5, wherein M represents zirconium.

18. The complex according to claim 6, wherein M represents zirconium.

19. The complex according to claim 4, wherein X in the formula (1) is a ligand comprising a conjugate base of 3-(methacryloyloxy)-1-propanesulfonic acid, and M represents hafnium.

20. The complex according to claim 6, wherein X in the formula (1) is a ligand comprising a conjugate base of carboxymethyl methacrylate, and M represents hafnium.

* * * * *